US00PP21798P2

(12) United States Plant Patent
Oostveen

(10) Patent No.: US PP21,798 P2
(45) Date of Patent: Mar. 22, 2011

(54) ***HIBISCUS* PLANT NAMED 'SPARKLE'**
(50) Latin Name: *Hibiscus moscheutos*
Varietal Denomination: Sparkle

(75) Inventor: Cornelis A. Oostveen, De Kwakel (NL)

(73) Assignee: De Zonnebloem Breeding B.V., De Kwakel (NL)

( * ) Notice: Subject to any disclaimer, the term of this patent is extended or adjusted under 35 U.S.C. 154(b) by 0 days.

(21) Appl. No.: 12/590,021

(22) Filed: Oct. 30, 2009

(51) Int. Cl.
*A01H 5/00* (2006.01)

(52) U.S. Cl. ..... Plt./257
(58) Field of Classification Search ..... Plt./257

See application file for complete search history.

*Primary Examiner*—Susan B McCormick Ewoldt
(74) *Attorney, Agent, or Firm*—C. A. Whealy

(57) ABSTRACT

A new and distinct cultivar of *Hibiscus* plant named 'Sparkle', characterized by its upright, somewhat, outwardly spreading and dense and bushy plant habit; dark green-colored leaves; freely flowering habit; large white-colored flowers with red purple-colored centers and venation; and good flower longevity.

2 Drawing Sheets

Botanical designation: *Hibiscus moscheutos.*
Cultivar denomination: 'SPARKLE'.

BACKGROUND OF THE INVENTION

The present invention relates to a new and distinct cultivar of *Hibiscus* plant, botanically known as *Hibiscus moscheutos,* and hereinafter referred to by the name 'Sparkle'.

The new *Hibiscus* plant is a product of a planned breeding program conducted by the Inventor in De Kwakel, The Netherlands. The objective of the breeding program is to create new compact *Hibiscus* plants with attractive and large flowers.

The new *Hibiscus* plant originated from a self-pollination in August, 2007 in De Kwakel, The Netherlands of *Hibiscus moscheutos* 'Mauvelous', not patented. The new *Hibiscus* plant was discovered and selected by the Inventor as a flowering plant within the progeny of the stated self-pollination in a controlled greenhouse environment in De Kwakel, The Netherlands in July, 2008.

Asexual reproduction of the new *Hibiscus* plant by vegetative terminal cuttings in a controlled greenhouse environment in De Kwakel, The Netherlands since May, 2009, has shown that the unique features of this new *Hibiscus* plant are stable and reproduced true to type in successive generations.

SUMMARY OF THE INVENTION

Plants of the new *Hibiscus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sparkle'. These characteristics in combination distinguish 'Sparkle' as a new and distinct cultivar of *Hibiscus:*

1. Upright, somewhat, outwardly spreading and dense and bushy plant habit.
2. Dark green-colored leaves.
3. Freely flowering habit.

4. Large white-colored flowers with red purple-colored centers and venation.
5. Good flower longevity.

Plants of the new *Hibiscus* can be compared to plants of the parent, 'Mauvelous'. Plants of the new *Hibiscus* differ primarily from plants of 'Mauvelous' in the following characteristics:

1. Plants of the new *Hibiscus* have slightly lighter green-colored leaves than plants of 'Mauvelous'.
2. Flowers of plants of the new *Hibiscus* and 'Mauvelous' differ in color as plants of 'Mauvelous' have pink-colored flowers.
3. Plants of the new *Hibiscus* have white-colored flower styles whereas plants of 'Mauvelous' have pale pink-colored flower styles.

Plants of the new *Hibiscus* can also be compared to plants of the *Hibiscus hybrida* 'Oak Red', filed concurrently in a U.S. Plant patent application. Plants of the new *Hibiscus* differ primarily from plants of 'Oak Red' in the following characteristics:

1. Plants of the new *Hibiscus* are more upright than plants of 'Oak Red'.
2. Plants of the new *Hibiscus* have ovate-shaped leaves whereas plants of 'Oak Red' have oakleaf-shaped leaves.
3. Flowers of plants of the new *Hibiscus* and 'Oak Red' differ in color as plants of 'Oak Red' have red-colored flowers.

BRIEF DESCRIPTION OF THE PHOTOGRAPHS

The accompanying colored photographs illustrate the overall appearance of the new *Hibiscus* plant, showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of typical flowering plants of 'Sparkle' grown in a container.

The photograph on the second sheet is a close-up view of a typical flower of 'Sparkle'.

DETAILED BOTANICAL DESCRIPTION

The aforementioned photographs and following observations, measurements and values describe plants grown in De Kwakel, The Netherlands in five-liter containers in a glass-covered greenhouses during the summer under conditions which closely approximate commercial *Hibiscus* production. During the production of the plants, day temperatures ranged from 18° C. to 33° C. and night temperatures ranged from 15° C. to 25° C. Plants were 16 weeks old when the photographs and the description were taken. In the description, color references are made to The Royal Horticultural Society Colour Chart, 2007 Edition, except where general terms of ordinary dictionary significance are used.

Botanical classification: *Hibiscus moscheutos* 'Sparkle'.

Parentage: Self-pollination of *Hibiscus moscheutos* 'Mauvelous,' not patented.

Propagation:

*Type.*—By vegetative terminal cuttings.

*Time to initiate roots, summer.*—About seven days at temperatures of 22° C.

*Time to initiate roots, winter.*—About ten days at temperatures of 19° C.

*Time to produce a rooted young plant, summer.*—About three weeks at temperatures of 21° C.

*Time to produce a rooted young plant, winter.*—About four weeks at temperatures of 18° C.

*Root description.*—Medium in thickness, fibrous; white to light brown in color.

*Rooting habit.*—Freely branching; dense.

Plant description:

*Plant and growth habit.*—Upright, somewhat outwardly spreading and dense and bushy plant habit; moderately vigorous growth habit.

*Branching habit.*—Freely branching, usually about 15 lateral branches develop; pinching enhances lateral branch development.

*Plant height.*—About 60.4 cm.

*Plant diameter* (*area of spread*).—About 77.5 cm.

Lateral branch description:

*Length.*—About 49.1 cm.

*Diameter.*—About 6 mm.

*Internode length.*—About 5.3 cm.

*Strength.*—Moderately strong.

*Texture.*—Smooth, waxy.

*Color.*—Between 144C and 145A with waxy layer close to 144D.

Foliage description:

*Arrangement.*—Alternate, single; numerous; symmetrical.

*Length.*—About 12.5 cm.

*Width.*—About 8.3 cm.

*Shape.*—Ovate.

*Apex.*—Apiculate.

*Base.*—Cordate.

*Margin.*—Crenate, slightly undulate.

*Texture, upper surface.*—Smooth, glabrous.

*Texture, lower surface.*—Densely pubescent.

*Venation pattern.*—Pinnate.

*Color.*—Developing leaves, upper surface: Close to 143A. Developing leaves, lower surface: Close to 138B. Fully expanded leaves, upper surface: Darker than N137D; venation, close to 144A and 144B. Fully expanded leaves, lower surface: Close to 147B; venation, close to 144B to 144C.

*Petiole.*—Length: About 8.6 cm. Diameter: About 3 mm. Texture, upper and lower surfaces: Smooth, glabrous. Color, upper and lower surfaces: Close to 145A.

Flower description:

*Flower arrangement.*—Large rotate flowers arranged singly at terminal leaf axils or in terminal clusters; uniform, continuous and freely flowering habit with numerous flower buds and/or open flowers per plant at one time; flowers face mostly upright to slightly outwardly.

*Fragrance.*—None detected.

*Flower longevity.*—Good flower longevity, flowers last for about four days; flowers not persistent.

*Natural flowering season.*—Plants flower from late summer until the autumn in The Netherlands.

*Flower diameter.*—About 18.5 cm.

*Flower length* (*height*).—About 5.6 cm.

*Flower bud.*—Rate of opening: Flowers buds open in about four days. Length: About 5.7 cm. Diameter: About 3.9 cm. Shape: Ovate. Color: Between 144B and 145A; towards the apex, close to 155A to 155B.

*Petals.*—Arrangement: Corolla consists of five petals that are fused at base; petals imbricate. Length: About 9.5 cm. Width: About 9.2 cm. Shape: Broadly obovate to flabellate. Apex: Rounded. Base: Attenuate. Margin: Entire. Texture: Smooth, glabrous. Color: When opening and fully opened, upper surface: Close to NN155C to NN155D; towards the base, close to 63B; venation, close to 63B; color becoming closer to 155C with development. When opening and fully opened, lower surface: Close to NN155C to NN155D; towards the base, close to 63B to 63C; venation, close to 63B to 63C.

*Sepals.*—Appearance: Five sepals fused into a tubular star-shaped calyx. Length: About 3.8 cm. Width: About 2.2 cm. Shape: Ovate. Apex: Acute. Margin: Entire. Texture, upper and lower surfaces: Smooth, glabrous. Color, immature, upper and lower surfaces: Close to 144B. Color, mature, upper surface: Between 144A and 145A. Color, mature, lower surface: Close to 143C.

*Peduncles.*—Length: About 4 cm. Diameter: About 2.5 mm. Angle: About 45° from the lateral branch axis. Strength: Moderately strong. Texture: Smooth, glabrous. Color: Close to 144A.

*Reproductive organs.*—Androecium: Stamen number: Numerous, about 120. Filament length: About 4 mm. Filament color: Close to 155D. Anther shape: Orbicular. Anther length: About 2 mm. Anther color: Close to 8D. Amount of pollen: Moderate. Pollen color: Close to 8B. Gynoecium: Pistil length: About 4.9 cm. Style length: About 4.1 cm. Style texture: Smooth, waxy. Style color: Close to 155D. Stigma appearance: Five-parted, rounded. Stigma color: Close to 160C to 160D. Ovary color: Close to 150C.

*Seeds/fruits.*—Seed and fruit development have not been observed.

Temperature tolerance: Plants of the new *Hibiscus* have been observed to have tolerate temperatures from about −20° C. to about 40° C.

Pathogen/pest resistance: Plants of the new *Hibiscus* have not been observed to be resistant to pathogens and pests common to *Hibiscus*.

It is claimed:

1. A new and distinct *Hibiscus* plant named 'Sparkle' as illustrated and described.

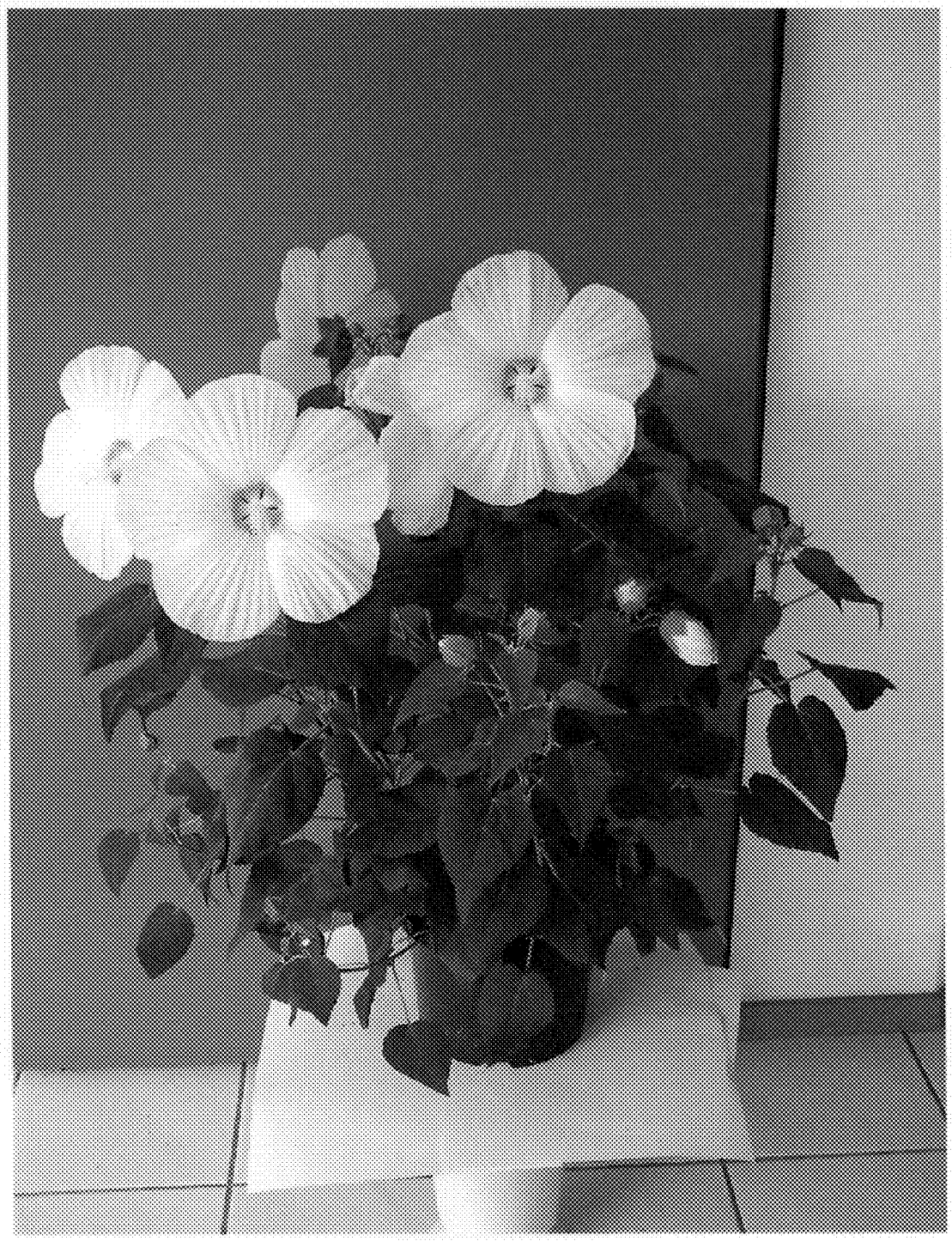

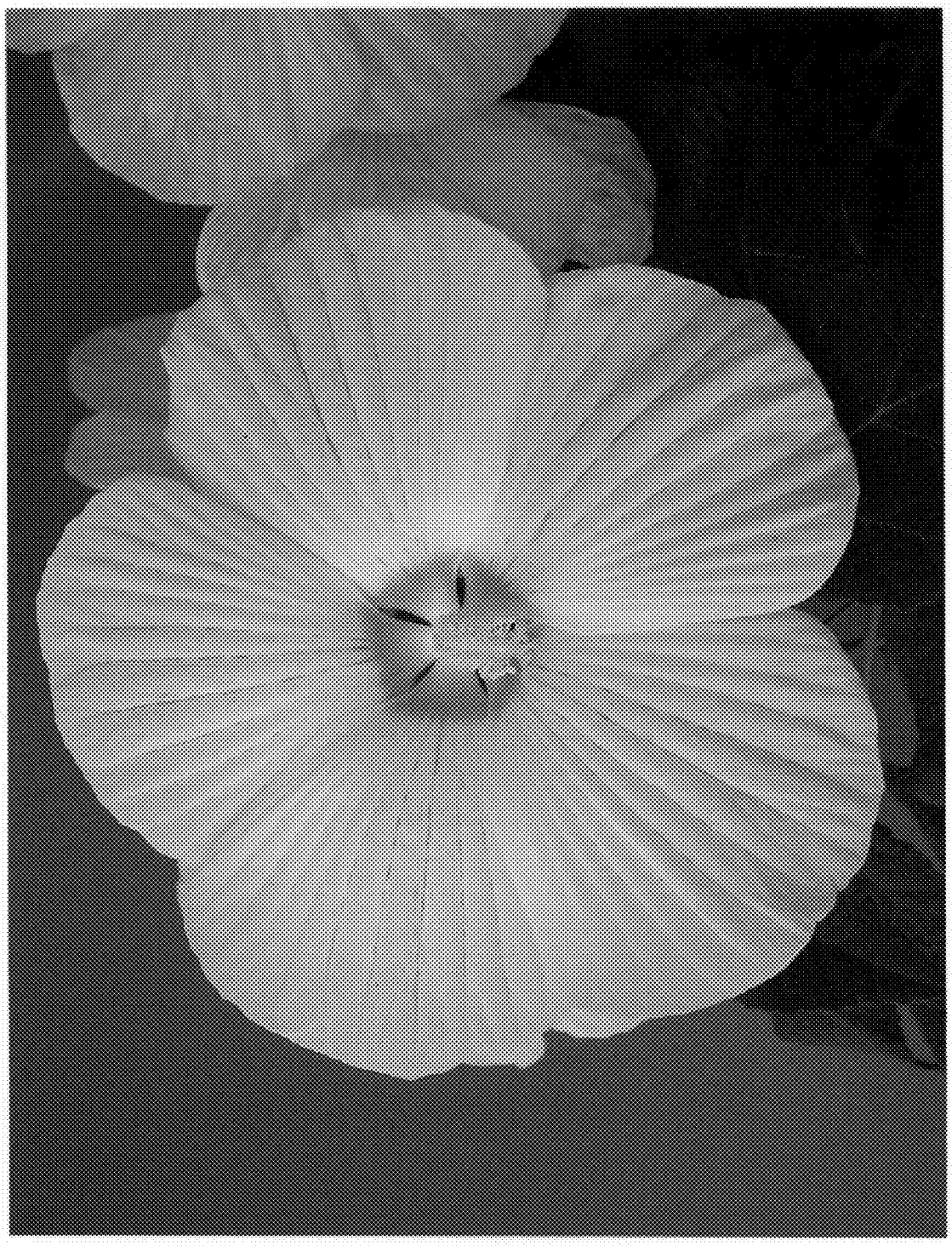

* * * * *